(12) United States Patent
Dimagno

(10) Patent No.: US 6,392,032 B1
(45) Date of Patent: May 21, 2002

(54) HEAVILY FLUORINATED SUGAR ANALOGS

(75) Inventor: Stephen G. Dimagno, Lincoln, NE (US)

(73) Assignee: Board of Regents University of Nebraska-Lincoln, Lincoln, NE (US)

(*) Notice: Subject to any disclaimer, the term of this patent is extended or adjusted under 35 U.S.C. 154(b) by 0 days.

(21) Appl. No.: 09/389,137

(22) Filed: Sep. 2, 1999

Related U.S. Application Data

(62) Division of application No. 08/937,672, filed on Sep. 25, 1997, now Pat. No. 6,013,790.
(60) Provisional application No. 60/026,459, filed on Sep. 25, 1996.

(51) Int. Cl.[7] .............................................. C07H 19/00

(52) U.S. Cl. .................... 536/28.2; 536/18.4; 536/18.5; 536/22.1; 536/28.53; 536/28.54; 536/28.55; 536/27.14

(58) Field of Search ............................ 536/18.4, 18.5, 536/22.1, 28.2, 123.1, 123.13, 27.14; 530/395

(56) References Cited

U.S. PATENT DOCUMENTS 6,013,790 A * 1/2000 Dimagno .................... 536/28.2

* cited by examiner

Primary Examiner—James O. Wilson
Assistant Examiner—Howard V Owens, Jr.
(74) Attorney, Agent, or Firm—Suiter & Associates PC

(57) ABSTRACT

Heavily fluorinated sugar analogs of formula

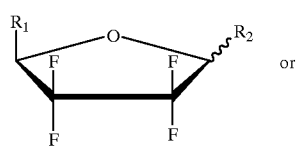

I

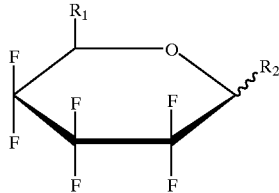

II wherein
$R_1$ is selected from alkyl, alkenyl, aryl, —$CH_2$—O-alkyl, —$CH_2$—O-aryl, —$CH_2OPO_3H$, —$CH_2$—O-carbohydrate, —$CH_2$—NH-peptide, or —$CH_2$—O-peptide;
wherein $R_2$ is selected from hydroxy, —O-carbohydrate, —NH-peptide,

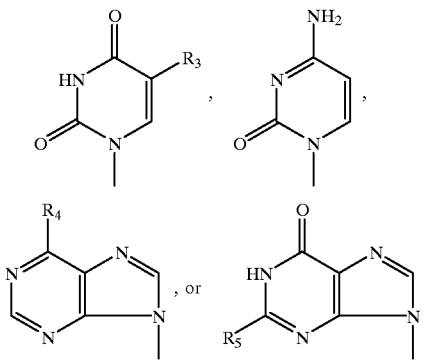

wherein
$R_3$ is selected from H, halogen, lower alkyl, lower alkenyl, lower haloalkyl, lower haloalkenyl, amino, mono- or di-lower alkylamino;
wherein $R_4$ is selected from amino, hydroxy, alkoxy, or halogen; and
wherein $R_5$ is H or amino. The compounds of formula (I) are useful as antiviral and antineoplastic agents and the compounds of formula (II) are useful as plant growth inhibitors and herbicides. Also disclosed is a method for preparing the heavily fluorinated sugars of the present invention which utilizes inexpensive starting materials which incorporate the desired number of fluorine moieties and a new reagent, benzyloxymethylzinc bromide, for introducing the 5'-hydroxymethyl moiety. The synthetic method of the present invention is advantageous in that it does not require late stage fluorination step.

40 Claims, 2 Drawing Sheets

US 6,392,032 B1

HEAVILY FLUORINATED SUGAR ANALOGS

RELATED APPLICATIONS

This is a divisional of U.S. application Ser. No. 08/937,672, filed Sep. 25, 1997, now U.S. Pat. No. 6,013,790, which claims priority under 35 U.S.C. §119(e) to U.S. provisional application Ser. No. 60/026,459, filed Sep. 25, 1996.

BACKGROUND OF THE INVENTION

1. Field of the Invention

The present invention relates to heavily fluorinated sugar molecules, a method for the preparation thereof, and their use as antiviral and antineoplastic agents, glycosidase inhibitors, plant growth regulators and herbicides, and as intermediates for the preparation of heavily fluorinated oligo- and polysaccharides. The present invention also relates to a new starting material for the preparation of the heavily fluorinated sugar analogs of the present invention.

2. Description of the Prior Art

Nucleotides perform a large number of functions for living organisms. For example, nucleotides serve as the basic building blocks for RNA and DNA, store and transfer the essential chemical energy that propels metabolism, activate chemical bonds for enzymatic reactions, control glycolysis, regulate the process of cell to cell communication, and perform a large number of other essential tasks. Because they are crucial to such a wide variety of essential biochemical tasks, nature has designed exquisitely selective enzymes for this class of compounds.

Neoplastic or viral diseases, in contrast to bacterial diseases, have proved difficult to treat. While bacterial diseases have a number of biochemical processes that are distinct to the organism, viruses use the cellular machinery of the infected host cell, and there are relatively few virus specific processes that can be inhibited selectively. Similarly, tumor cells are mutated variants of normal cells and rely on many of the same biochemical pathways. Therefore, chemotherapies targeted for these diseases are often highly toxic due to the lack of selectivity of the compound for diseased cells. One characteristic that marks both virally infected cells and tumor cells is their propensity for rapid growth. Since growth involves synthesis of DNA and RNA, these cells require a greater flux of nucleotides in comparison to normal cells, and often the diseased cell contains enzymes which are less selective for nucleotides than their counterparts in normal cells. Therefore, nucleotide analogs may act as substrates for the disease state enzymes, while they are virtually ignored by normal enzymes. This is the rationale for design of therapeutic nucleotide or nucleoside analogs, such as IUDR, trifluorothymidine, AZT, Ara-A, ribavirin, acyclovir, ganciclovir, gemcitabine, MDL-101,731. Research on derivatives of nucleoside and nucleotide analogs continues to be intense. As the above examples show, modification on the base and sugar moieties is possible and in some case, desirable. Recently, there has been a great deal of interest in fluorinated derivatives in which fluorine is incorporated into the sugar nucleus. Gemcitabine (Eli Lilly) is now heading to market as an antiviral as well as a treatment for non small cell lung cancer. Pancreatic cancer studies are also underway. The fluorine substituents help stabilize the sugar against glycolysis and improve the oral bioavailability of the drug. MDL 101,731 is active against breast, prostate, and colon cancers. Although nucleoside analogs containing fluorine in the sugar nucleus are known in the art, such as gemcitabine and MDL-101,731, the prior art compounds only contain one or two fluorine substituents. See also U.S. Pat. No. 4,963,662 (Matthes et al.), U.S. Pat. No. 5,153,180 (Matthes et al.), and U.S. Pat. No. 4,762,823 (Watannabe et al.).

SUMMARY OF THE INVENTION

It is an object of the present invention to provide heavily fluorinated sugar analogs containing a tetrafluoroethylene unit (—$CF_2CF_2$—) in the sugar nucleus of ribose based nucleoside analogs and a hexafluorotrimethylene unit (—$CF_2CF_2CF_2$—) in the sugar nucleus of hexose based nucleoside analogs.

Another object of the present invention is to provide a synthetic method for easily obtaining the heavily fluorinated sugar analogs which provides for a higher degree of fluorination than is obtainable in the prior art methods, and which does not require a fluorination step at or near the end of the synthesis.

Another object of the present invention is to provide a novel starting material for the production of heavily fluorinated sugars.

Yet another object of the present invention is to provide a method for the treatment of viral and neoplastic diseases by administering a pharmaceutically effective amount of the heavily fluorinated nucleoside analogs according to the present invention to a patient in need thereof.

A further object of the present invention is to provide for a method of inhibiting glycosidases by administering a pharmaceutically effective amount of the heavily fluorinated nucleoside analogs according to the present invention to a patient in need thereof, such as a patient with diabetes mellitus.

DETAILED DESCRIPTION OF THE INVENTION

Figure 1:
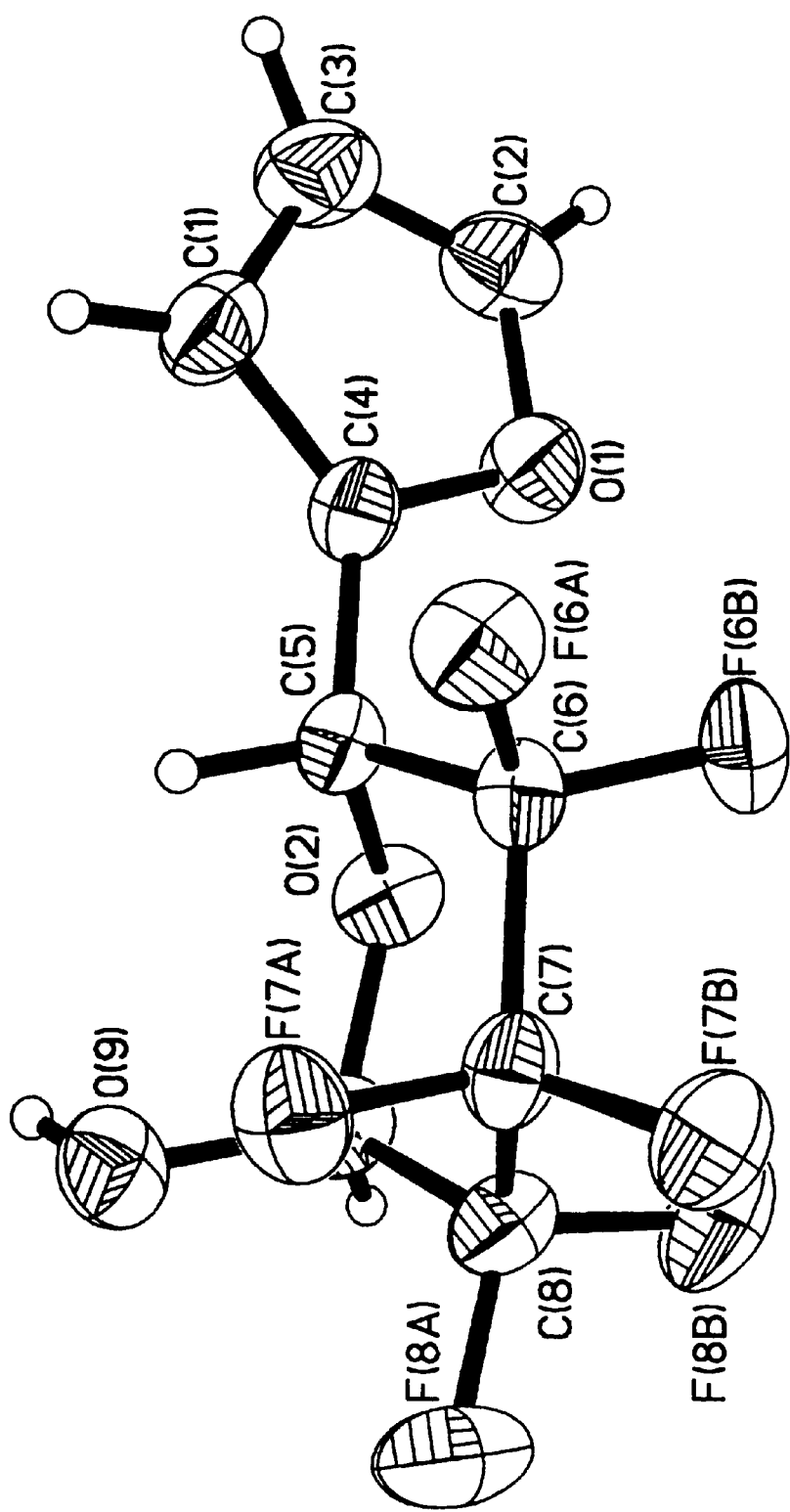
FIG. 1 shows an x-ray crystal determination of compound 2.

The objects of the present invention are provided by the heavily fluorinated sugar analogs of formula:

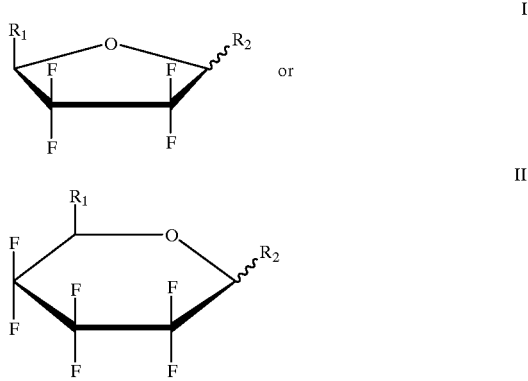

wherein
 $R_1$ is selected from alkyl, alkenyl, aryl, —$CH_2$—O-alkyl, —$CH_2$—O-aryl, —$CH_2OPO_3H$, —$CH_2$—O-carbohydrate, —$CH_2$—NH-peptide, or —$CH_2$—O-peptide;
 wherein $R_2$ is selected from hydroxy, —O-carbohydrate, —NH-peptide,

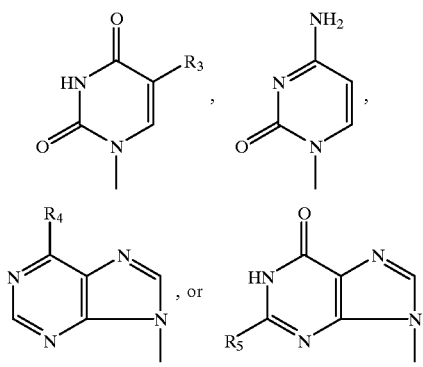

wherein
R₃ is selected from H, halogen, lower alkyl, lower alkenyl, lower haloalkyl, lower haloalkenyl, amino, mono- or di-lower alkylamino;
wherein R₄ is selected from amino, hydroxy, alkoxy, or halogen; and
wherein R₅ is H or amino.

The compounds according to the present invention are intended to encompass all stereoisomers and mixtures thereof.

Halogen includes fluorine, chlorine, bromine, or iodine. Lower alkyl includes branched or straight chain alkyl groups having from 1 to about 10 carbon atoms. Lower haloalkyl includes branched or straight chain alkyl groups having from 1 to about 10 carbon atoms mono-, di-, or trisubstituted, or higher, by fluorine, chlorine, bromine, or iodine, such as monofluoromethyl, difluoromethyl, trifluoromethyl, etc. Lower alkenyl includes branched or straight chain alkenyl groups having from 1 to about 10 carbon atoms, having one or more carbon-carbon double bonds. Lower haloalkenyl includes branched or straight chain alkenyl groups having from 1 to about 10 carbon atoms having one or more carbon-carbon double bonds mono-, di-, or trisubstituted, or higher, by fluorine, chlorine, bromine, or iodine. Typical carbohydrates in the definition of R₁ and R₂ include, for example, mono-, di-, oligo-, or polysaccharides, such as glucose, galactose, and the like. Typical peptides in the definition of R₁ and R₂ include, for example, naturally occurring or synthetic amino acids, or di-, oligo-, or polypeptides, derived from naturally occurring or synthetic amino acids.

The compounds according to the present invention according to formula (I) find utility as antiviral and antineoplastic agents, and as glycosidase inhibitors. The compounds according to formula (II) are useful as plant growth inhibitors, glycosidase inhibitors, and herbicides.

A further aspect of the present invention relates to processes for preparing heavily fluorinated sugars and starting materials and intermediates useful therein.

It will be understood that the reactions in which the novel heavily fluorinated carbohydrates according to the present invention are coupled with the bases are frequently of a nature such that the hydroxy groups should be protected to keep them from reacting with the base, or being decomposed in some manner. The protecting groups are chosen from the groups used in synthetic organic chemistry for the purpose. Chemists are accustomed to choosing groups which can be efficiently placed on hydroxy groups, and which can be easily removed when the desired reaction is complete. Suitable groups are described in standard textbooks, such as Chapter 3 of Protective Groups in Organic Chemistry, McOmie, Ed., Plenum Press, New York (1973); and Chapter 2 of Protective Groups in Organic Synthesis, Greene, John Wiley & Sons, New York (1981).

Typical hydroxy-protecting groups include formyl, 2-chloroacetyl, benzyl, diphenylmethyl, triphenylmethyl, 4-nitrobenzyl, phenoxycarbonyl, t-butyl, methoxymethyl, tetrahydropyranyl, allyl, tetrahydrothienyl, 2-methoxyethoxymethyl, methoxyacetyl, phenoxyacetyl, isobutyryl, ethoxycarbonyl, benzyloxycarbonyl and the like. Silyl hydroxy-protecting groups are often particularly convenient, because most of them are easily cleaved by contact with water or an alcohol. Such groups include especially trimethylsilyl, as well as isopropyldimethylsilyl, methyldiisopropylsilyl, triisopropylsilyl, t-butyldimethylsilyl, and the like.

Heavily fluorinated carbohydrates may have a hydroxy group at the 1-position of its ring, and in order to react the heavily fluorinated sugars with a base to form the heavily fluorinated nucleoside analogs according to the present invention, it is necessary to place a leaving group at the 1-position. The leaving groups used are typical of those used commonly in organic synthesis. The preferred leaving groups are sulfonates, of which the most preferred is methanesulfonate; other typical leaving groups such as toluenesulfonate, ethanesulfonate, isopropanesulfonate, 4-methoxybenzenesulfonate, 4-nitrobenzenesulfonate, and 2-chlorobenzenesulfonate. Chloro and bromo may also be used.

An appropriate leaving group may be placed at the 1-position of the heavily fluorinated sugar. The preferred leaving group is methanesulfonyl, which may be readily provided by reaction with methanesulfonyl chloride in the presence of an equivalent amount of a suitable acid scavenger such as triethylamine and the like. Other sulfonyl leaving groups may be provided in the same way by reaction with the appropriate sulfonyl halide.

The purine and/or pyrimidine bases used to form the heavily fluorinated nucleoside analogs according to the present invention are commonly known to those skilled in the art, and no discussion of their synthesis is necessary. However, the primary amino groups which are present on some of the bases should be protected before the base is coupled with the heavily fluorinated sugars. The usual amino-protecting groups are used, including silyl groups such as have been discussed, as well as such typical groups as t-butoxycarbonyl, benzyloxycarbonyl, 4-methoxybenzyloxycarbonyl, 4-nitrobenzyloxycarbonyl, formyl, acetyl, and the like.

It is often advisable to convert keto oxygen atoms on the bases to the enol form, in order to make the bases more highly aromatic and thereby allow more ready attack of the base by the carbohydrate. It is most convenient to enolize the oxygens by providing silyl protecting groups for them. The usual silyl protecting groups as discussed above are used for this purpose, also.

The reaction between the protected heavily fluorinated sugar and the base may be carried out neat at an elevated temperature in the range of from about 50° C. to about 200° C. It is also possible to use relatively high-boiling solvents for the reaction, such as dimethylformamide, dimethylacetamide, hexamethylphosphoramide and the like. However, if the coupling reaction is carried out under elevated pressure, to avoid distillation of a low-boiling solvent, any convenient inert reaction solvent can be used.

The coupling reaction may be done at low temperatures if a reaction initiator, such as a trifluoromethanesulfonyloxysilane, is used. The usual inert reaction solvents, such as tetrahydrofuran, diethyl ether, halogenated alkanes such as chloroform, dichloromethane, trichloroethane and the like, and aromatics including such solvents as benzene, toluene and the xylenes may be used.

The final step of the reaction sequence is the removal of the protecting groups. Most silyl protecting groups may be easily cleaved by contact with water or an alcohol. The t-butyldimethylsilyl protecting group requires acid conditions, such as contact with gaseous hydrogen halide, for its removal.

Acyl protecting groups may be removed by simple hydrolysis with strong or moderately strong bases, such as alkali metal hydroxides, at temperatures from about the ambient temperature to about 100° C. Such hydrolyses may be conveniently carried out in hydroxylic solvents, especially aqueous alkanols. The reactions may also be carried out in any convenient solvent, such as polyols including ethylene glycol, ethers such as tetrahydrofuran and the like, ketones such as acetone and methyl ethyl ketone and other polar solvents such as dimethylsulfoxide. The cleavage of acyl protecting groups may also be performed with other bases, including, for example, sodium methoxide, potassium t-butoxide, hydrazine, hydroxylamine, ammonia, alkali metal amides and secondary amines such as diethylamine and the like. The acyl protecting groups can also be removed with acid catalysts, such as methanesulfonic acid, hydrochloric acid, hydrobromic acid, sulfuric acid, or with acidic ion exchange resins. The removal of protecting groups which are ethers is carried out by known methods, for example, with ethanethiol and aluminum chloride.

A preferred synthetic method for preparing compounds and intermediates according to the present invention is described below.

Heavily fluorinated sugar derivative of Formula (III):

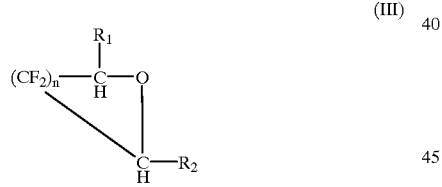

(III)

wherein $R_1$ is selected from alkyl, alkenyl, aryl, —$CH_2$—O-alkyl, —$CH_2$—O-aryl, —$CH_2OPO_3H$, —$CH_2$—O-carbohydrate, —$CH_2$—NH-peptide, or —$CH_2$—O-peptide;

wherein $R_2$ is selected from hydroxy, —O-carbohydrate, —NH-peptide,

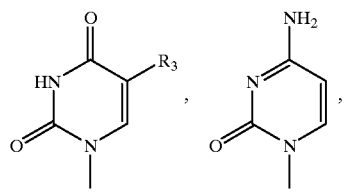

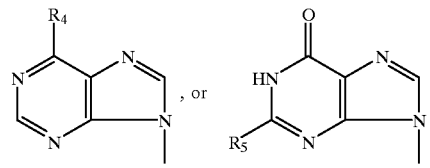

wherein $R_3$ is selected from H, halogen, lower alkyl, lower alkenyl, lower haloalkyl, lower haloalkenyl, amino, mono- or di-lower alkylamino;

wherein $R_4$ is selected from amino, hydroxy, alkoxy, or halogen;

wherein $R_5$ is H or amino; and wherein n=2 or 3;

may be prepared by converting one of the carboxylic ester groups of Formula (IV):

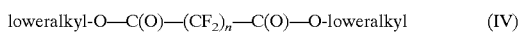

loweralkyl-O—C(O)—$(CF_2)_n$—C(O)—O-loweralkyl    (IV)

wherein n=2 or 3, to the ketone to yield compounds of Formula (V):

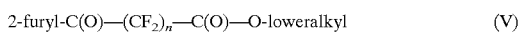

2-furyl-C(O)—$(CF_2)_n$—C(O)—O-loweralkyl    (V)

and then contacting a compound of Formula (V) with a reducing agent to form compounds of Formula (VI):

(VI)

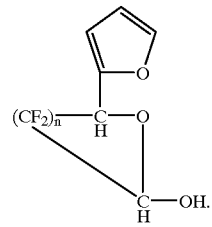

The hydroxy group of the compound of Formula (VI) may be protected with a protecting group to form compounds of Formula (VII):

(VII)

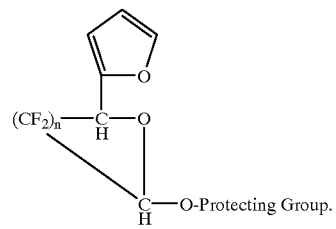

The furyl group is converted to the carboxyl group by oxidation, to form compounds of Formula (VIII):

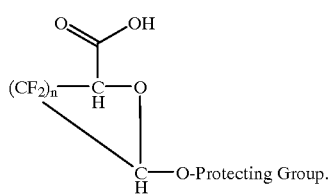

(VIII)

The carboxyl group of compounds of Formula (VIII) may be reduced to a hydroxymethyl group to form compounds of Formula (IX):

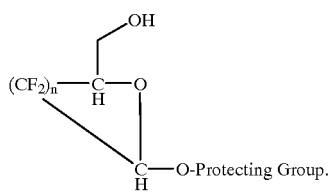

(IX)

The protecting group of the compounds of Formula (IX) may be removed to produce compounds of Formula (X):

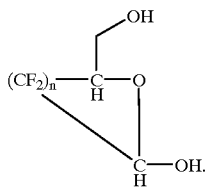

(X)

Alternatively, the hydroxy group of the compound of Formula (IX) may also be protected to form compounds of Formula (XI):

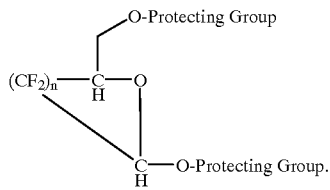

(XI)

These procedures are general and can be successfully used for the introduction of any R-group in the terminal position. Examples include those shown in Formula (XII):

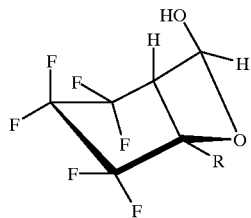

wherein R is alkyl, alkenyl, aryl, $CH_2$O-alkyl, $CH_2$O-aryl, $CH_2OPO_3H_2$, $CH_2$O-carbohydrate, $CH_2$NH-peptide, or $CH_2$O-peptide.

Additionally, essentially any carbohydrate residue or amino acid or peptide residue can be introduced at the 1-position to form the compounds of formula (XIII):

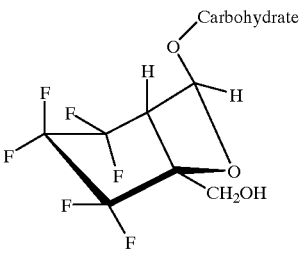

or Formula (XIV):

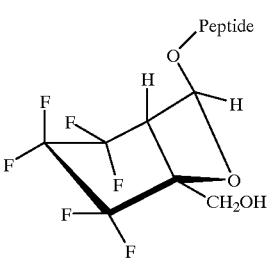

These general procedures are employed in the preparation of the compounds of the present invention in the Examples below. Moisture sensitive reactions were run under a nitrogen atmosphere using oven dried Schlenk-type glassware. Commercially available high grade purity reagents were used without further purification. THF was distilled from Na and benzophenone, $CH_2Cl_2$ was distilled from $CaH_2$. TEA and DEA were stored over molecular sieves and KOH, respectively. Analytical samples were obtained by preparative TLC using Whatman PK5F silica plates with fluorescent indicator or by recrystallization. Deuterated chloroform and acetone were stored over basic alumina and filtered through sand directly in the sample tube. Melting points are uncorrected.

NMR Spectroscopy data is reported in the following Examples as follows. Since compounds 2, 3, 4, 5, and 7 can be obtained in high de following the experimental protocol, and the two cis and trans-1,5 diastereomers cannot be separated by simple column chromatography, the NMR data are reported for the major diastereomer only. HETCOR, COSY, $^1H$, $^{13}C$, $^{19}F$, $^{19}F$ decoupled $^1H$, $^1H$ decoupled $^{19}F$, and $^{19}F$ decoupled $^{13}C$ experiments were run on a 500 MHz General Electric instrument. $^1H$ NMR were also run on a 360 MHz Tecmag-Nicolet instrument. Standard resolution enhancement algorithms were applied to the $^1H$, $^{13}C$, $^{19}F$, and cross-decoupled spectra. When the assignment of $CF_2$ mutiplicity on the $^{13}C$ is complicated by the presence of overlapping signals, and/or low s/n ratio the chemical shift is given based on $^{19}F$ decoupled $^{13}C$ data.

The following preparations and examples further illustrate the synthesis of compounds of the present invention.

Diethyl 2,2,3,3,4,4-hexafluoropentanoate. Large quantities of commercially available diester was prepared using standard esterification procedure from the corresponding diacid. An ethanol solution (250 mL) containing 2,2,3,3,4,4-hexafluoroglutaric acid (11.23 g, 47.0 mmol) and concentrated sulfuric acid (5 mL) was refluxed for 7 days using a soxlet apparatus and 4 Å activated molecular sieves (1.6 mm pellets) for water removal. At the end of this period ethanol was removed in vacuo and the residue was neutralized to pH 7 with $NaHCO_3$ powder before adding water (250 mL). The solution was transferred in a separatory funnel and the product was extracted with ether (3×100 mL). The combined ether extracts were washed with water (75 mL), pre-dried with brine (75 mL), then dried over $MgSO_4$ and filtered. After ether removal, the crude pale yellow liquid was subjected to vacuum transfer (0.5 mmHg, 60–80° C.). Diethyl 2,2,3,3,4,4-hexafluoroglutarate was obtained as a clear, low viscosity liquid (11.34 g, 81%). $^1H$ NMR (360 MHz $CDCl_3$) δ1.38 (6H, t, J=7.2 Hz), 4.41 (4H, q, J=7.2 Hz).

Ethyl 5-(2-furyl)-5-oxo-2,2,3,3,4,4-hexafluoropentanoate (1). The following steps were performed in the absence of light. A solution of furan (0.9 mL, 12.4 mmol), in THF (30 mL) was cooled to −78° C. prior to the addition of n-BuLi (3 mL, 2.5 M in hexane, 7.5 mmol). The mixture was stirred at room temperature for 3 h. The resulting 2-lithiofuran solution was added to a −78° C. solution of diethyl 2,2,3,3,4,4-hexafluoropentanoate (4.1 g, 13.8 mmol) in THF (100 mL) over a 15 min period and allowed to stir for 30 min. Warm up and simultaneous in vacuo removal of solvent followed at the end of the stirring period. The yellow-red crude mixture was immediately purified with column chromatography on silica gel. The diester was recovered during elution with hexanes and a 9:1 hexanes:EtOAc mixture (1.64 g, 39% recovery). The UV active product 1 (1.53 g, 64% calcd from nBuLi), as a yellow oil, eluted with a 8:2 hexanes:EtOAc combination. $^1H$ NMR (360 MHz, $CDCl_3$, $^1H$-$^{19}F$ HETCOR cross peak) δ1.37 (3H, t, J=7.2 Hz), 4.43 (2H, q, J=7.2 Hz), 6.65 (1 H, dd, J=3.7, 1.6 Hz), 7.50 (1H, m), 7.80 (1H, d, J=1.6 Hz). $^{13}C$ NMR (125 MHz, $CDCl_3$) δ13.9, 65.2, 108.7 (tt, $J_{C-F}$=266.4, 31.4 Hz, $CF_2$), 110.9 (tt, $J_{C-F}$=266.4, 33.3 Hz, $CF_2$), 111.0 (tt, $J_{C-F}$=266.4, 31.4 Hz, $CF_2$), 113.92, 125.6, 148.5, 151.0, 159.2 (t, $J_{C-C-F}$=29.6 Hz), 171.4 (t, $J_{C-C-F}$=27.8 Hz). $^{19}F$ NMR (470 MHz, $CDCl_3$) δ−123.40 (2F, s), −118.69 (2F, t, J=10.0 Hz), −116.98 (2F, t, J=10.0 Hz). Anal. Calcd. for $C_{11}H_8F_6O_4$: C, 41.53; H, 2.53. Found: C, 41.80; H, 2.66.

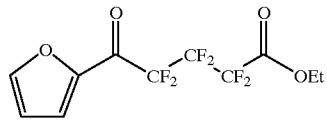

(1)

1-Hydroxy-5-(2-furyl)-2,2,3,3,4,4-hexafluorooxane (2). Sodium borohydride (0.35 g, 9.25 mmol) was added to a stirred solution of 1 (1.53 g, 4.81 mmol) in anhydrous methanol (100 mL) at 0° C. After a 3 h period at that temperature, the solvent was removed using a rotoevaporator and the residue acidified to pH 2 with 2N HCl. The aqueous mixture was then neutralized with saturated $NaHCO_3$ prior to an extraction with ether (3×50 mL). The combined organic layers were dried with $MgSO_4$ and concentrated. Product 2 (1.28 g, 96%) was obtained as a viscous dark-yellow oil which was a 1:1 mixture of trans:cis-1,5-(2) diastereomers. The oil crystallized after standing undisturbed for a 2 h period. Recrystallization from an anhydrous, acid-free 3:1 hexane:$CHCl_3$ solution afforded X-ray quality crystals mp=89–90° C. in quantitative yield. The X-ray structure revealed that the cis-2 diastereomer had undergone ring opening and closing to the crystal-forming trans-2 unit. The X-ray crystal structure determination of 2 is shown in FIG. 1. The trans-2 racemate is clearly visible in the centrosymmetric unit cell. Exclusion of water from the NMR solvent prevents the ring opening in solutions and allows to record spectra of the single anomer. $^1H$ NMR of trans-2 (500 MHz, $CDCl_3$, $^1H$-$^{19}F$ HETCOR cross peak) δ3.60 (1H, s), 5.45 (1H, s), 5.52 (1H, d, J=23 Hz), 6.47 (1H, dd, J=3.2, 2.0 Hz), 6.67 (1H, d, J=3.2 Hz), 7.51 (1H, d, J=1.2 Hz). $^{13}C$ NMR of trans-2 (125 MHz, $d_6$-Acetone) δ64.2 (ddd, $J_{C-C-F}$=25.9, 18.5, 3.7 Hz), 91.5 (dd, $J_{C-C-F}$=38.8, 24.1 Hz), 109.0 ($CF_2$), 111.0, 110.8 ($CF_2$), 113.9 ($CF_2$), 112.6, 143.3, 144.3. $^{19}F$ of trans-2 (470 MHZ, $d_6$-Acetone, $^{19}F$-$^{19}F$ COSY cross peak) δ−143.9 (i1, dddddd, J=272.2, 13.8, 9.6, 6.0 Hz), −132.0 (1F, ddt, J=274.2, 10.1, 10.0 Hz), −130.4 (1F, dtddd, J=264.2, 9.4, 8.9, 4.71, 1.4 Hz), −128.22 (1F, ddt, J=264.2, 15.0, 10.0 Hz), −125.6 (1F, ddddd, J=272.2, 7.3 Hz), −121.6 (1F, ddtd, J=274.2, 16.8, 7.0 Hz). Anal. Calcd for $C_9H_6F_6O_3$: C, 39.15; H, 2.19. Found: C, 39.25; H, 2.34.

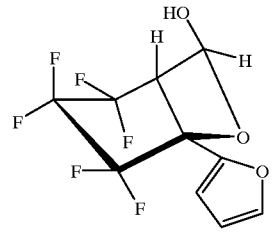

(2)

1-O-Benzyloxy-5-(2-furyl)-2,2,3,3,4,4-hexafluorooxane (3). Benzoyl chloride (1.16 mL, 10.0 mmol) and TEA (3.0 mL, 20 mmol) were added dropwise simultaneously to a solution of crystalline 2 (2.32 g, 8.41 mmol) in 50 mL of $CHCl_2$ at room temperature. The mixture was stirred at that temperature for 15 min before quenching with excess diethylamine. After an additional 15 min period the solvent was removed and the residue was immediately poured onto a silica gel column and eluted with a 9:1 hexane:EtOAc mixture. This operation efficiently removed the impurities in the form of triethylammonium chloride and N,N-diethyl benzamide giving the clear heavy oil 3 (3.11 g, 97%) as a 15:1 mixture of tris:cis 1,5-disubstituted oxane by NMR. The mixture was carried to the next step without further purification. $^1H$ NMR of trans-3 (500 MHz, $CDCl_3$) δ5.20 (1H, dd, J=20.9, 3.62 Hz), 6.37 (1H, dd, J=15.31, 3.62 Hz), 6.45 (1H, dd, J=3.23, 1.62 Hz), 6.70 (1H, d, J=3.23 Hz), 7.50 (3H, m), 7.64 (1H, m), 8.13 (2H, dd, J=8.06, 1.21 Hz). $^{13}C$ NMR of trans-3 (125 MHz, $CDCl_3$) δ70.53 (ddd, $J_{C-C-F}$= 22.2, 18.5, 3.7 Hz), 88.7 (ddd, $J_{C-C-F}$= 29.6, 18.5, 5.6 Hz), 109.0 (ddtt, $J_{C-F}$=283.0, 253.4, 29.6, 22.2 Hz, $CF_2$), 110.5 (ddddd, $J_{C-F}$=268.2, 260.8, 27.8, 24.0, 3.7 Hz, $CF_2$), 111.0, 111.6 (ddddd, $J_{C-F}$=268.2, 260.8, 27.7, 24.0, 3.7 Hz, $CF_2$) 112.7, 127.4, 128.7, 130.5, 134.6, 142.4, 144.5, 163.5. $^{19}F$ NMR of trans-3 (470 MHz, $CDCl_3$) δ−145.9 (1F, dtt, J=274.7, 15.3, 4.4 Hz), −137.0 (1F, dtd, J=263.8, 17.4, 8.7 Hz), −133.6 (1F, ddt, J=261.6, 15.3, 8.7 Hz), −130.3 (1F, dm, J=266.4 Hz), 429.0 (1F, ddt, J=265.9, 13.1, 10.9 Hz), −126.9 (1F, dm, J=272.7 Hz). Anal. Calcd. for $C_{16}H_{10}F_6O_4$: C, 50.41; H, 2.65. Found: C, 50.76; H, 2.48.

(3)

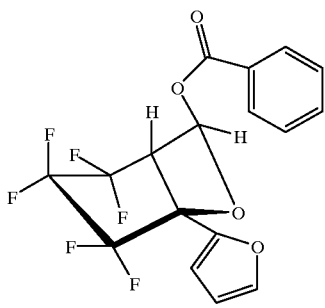

5-O-Benzyloxy-2,2,3,3,4,4-hexofluorooxanoic acid (4). Oxidative removal of furyl was effected using $RuO_2$ (5 mol %) that was added to a biphasic solution of water (180 mL), acetonitrile (60 mL), and $CCl_4$ (120 mL) containing 3 (2.93 g, 7.71 mmol) and $NaIO_4$ (24.7 g, 116 mmol). The grey mixture was stirred vigorously for 5 days while monitored by TLC. The volatile solvents were removed and the aqueous residue extracted with EtOAc (3×150 mL) and dried with $MgSO_4$, filtered through celite and activated carbon. Solvent removal in vacuo cleanly afforded 4 as a white solid (2.65 g, 96% wet yield). $^1H$ NMR (500 MHz, $d_6$-Acetone) δ3.6 (broad S, OH), 5.48 (1 H, dmult, J=21.4 Hz), 6.59 (1H, dd, J=14.9, 3.62 Hz), 7.62 (2H, m), 7.78 (1H, m), 8.12 (2H, m). Anal. Calcd. for $C_{13}H_8F_6O_5$: C, 45.59; H, 2.25. Found: C, 43.00; H, 2.25. The elemental analysis data shows the presence of $H_2O$ even after extensive drying. A small amount of the hygroscopic acid product was quantitatively converted into the methyl ester derivative methyl 5-O-benzyloxy-2,2,3,3,4,4-hexafluorooxanoate (4a) by standard titration with diazomethane in ether solution, and then fully characterized. $^1H$ NMR of 4a (500 MHz, ($CDCl_3$) δ3.87 (3H, s), 4.71 (1H, m), 6.25 (1H, dd, J=14.5, 3.63 Hz), 7.50 (2H, m), 7.66 (1H, m), 8.12 (2H, m). $^{13}C$ NMR of 4a (125 MHz, $CDCl_3$) δ53.6, 72.1 (t, $J_{C-C-F}$=25.9 Hz), 88.2 (ddd, $J_{C-C-F}$=22.2, 18.5, 3.7 Hz), 108.5 (ddtt, $J_{C-F}$=281.2, 253.4, 29.6, 20.3 Hz, $CF_2$), 110.1 (tdd, $J_{C-F}$=266.4, 29.6, 22.2 Hz, $CF_2$), 111.2 (tdd, $J_{C-F}$=257.1, 25.9, 20.5 Hz, $CF_2$), 127.2, 128.8, 130.6, 134.7, 161.7, 163.4. $^{19}F$ NMR (470 MHz, $CDCl_3$) δ−145.4 (1F, ddquart, J=273.6, 12.7 Hz), −136.8 (1F, dddtd, J=261.0, 14.7, 7.5, 2.4 Hz), −133.6 (1F, dddt, J=263.0, 15.4, 9.3, 5.8 Hz), −128.1 (2F, m), −126.7 (1F, dm, J=273.6 Hz). HRMS (EI) m/z calcd for $C_{14}H_{10}F_6O_5$ 372.0432, found 372.0434.

(4)

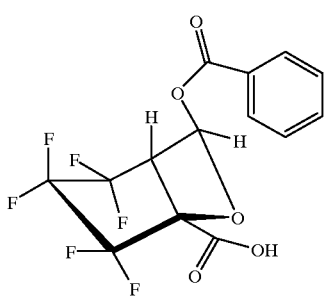

1-O-Benzyloxy-5-(5'-hydroxymethyl)-2,2,3,3,4,4-hexafluorooxane (5). A solution of 4 (2.3 g, 6.42 mmol) in THF (20 mL) at 0° C. was treated with 1M $BH_3$-THF complex (39 mL). The mixture was stirred at 0° C. for 20 min, then at room temperature for 24 hr in a closed system. At the end of that period 1M DIBAL-H in THF (19 mL), was added to the reaction mixture at room temperature and stirred for 30 min. The reaction was quenched with $H_2O$ (20 mL) at 0° C., treated with 20 mL 2M HCl, then neutralized with $NaHCO_3$ before extraction with EtOAc (3×150 mL). The organic extracts were dried with $MgSO_4$, filtered and concentrated. The crude clear heavy oil was purified by flash chromatography on silica with a 10:1 mixture of hexane:ethyl acetate. Pure 5 (1.814 g, 82%) was obtained as a pale yellow solid. $^1H$ NMR (500 MHz, $CDCl_3$) δ2.05 (1H, dd, J=8.5, 5.2 Hz), 4.02 (2H, m), 4.19 (1H, ddddd, J=20.1, 3.6Hz), 6.20 (1H, dd, J=11.3, 3.6 Hz), 7.50 (2H, m), 7.66 (1H, m), 8.13 (2H, m). $^{13}C$ NMR (125 MHz, $CDCl_3$) δ58.3, 74.6 (dd, $J_{C-C-F}$=27.7, 24.0 Hz), 88.7 (ddd, $J_{C-C-F}$=29.6, 18.5, 5.5 Hz), 108.5 (ddtt, $J_{C-F}$=283.0, 253.4, 29.6, 20.3 Hz, $CF_2$), 110.4 (dddd, $J_{C-F}$=270.1, 264.5, 27.7, 24.0 Hz, $CF_2$), 112.2 (dddd, $J_{C-F}$=270.1, 264.5, 27.7, 24.0 Hz, $CF_2$), 127.3, 128.8, 130.4, 134.7, 163.7. $^{19}F$ NMR (470 MHz, $CDCl_3$) δ−146.7 (1F, dtt, J=273.3, 13.9, 9.7 Hz), −137.1 (1F, dqdt, J=262.2, 15.3, 8.3, 2.8 Hz), −134.0 (1F, dm, J=262.2 Hz), −132.4 (1F, ddtd, J=267.7, 13.9, 6.9, 4.2 Hz), −131.5 (1F, dm, J=266.4 Hz), −127.2 (1F, dm, J=269.1 Hz). Anal. Calcd. for $C_{13}H_{10}F_6O_4$: C, 45.36; H, 2.93. Found: C, 45.47; H, 2.91.

(5)

1-Hydroxy-5-(5'-hydroxymethyl)-2,2,3,3,4,4-hexafluorooxane (6). A solution of 5 (0.497 g, 1.44 mmol) and $K_2CO_3$ (65 mg, 0.47 mmol) in trifluoroethanol (20 mL) was stirred at room temperature for 12 h. After solvent removal, saturated $NaHCO_3$ solution was added to the residue. The aqueous layer was extracted with pentane (3×50 mL) then acidified to pH 2 with 2N HCl followed by extraction with AcOEt (3×60 mL). The AcOEt extract was dried with $MgSO_4$ and concentrated to yield 6 (0.347 g, 99% crude) as a colorless heavy oil which crystallized during in vacuo removal of solvent. The product was recrystallized from a 2:1 hexanes:$Et_2O$ solution. The normal protocol followed in the NMR sample preparation was not sufficient to prevent equilibration of the cis and trans diastereomers in solution. Qualitatively, compound 6 was soluble in acetone, EtOAc, ether, and water; insoluble in $CHCl_3$ and other solvents of lower polarity. $^1H$ NMR of cis 1,5-(6) (500 MHz, $d_6$-Acetone, $^1H$-$^{19}F$ HETCOR cross peaks) δ3.82 (1H, dddd, J=12.1, 6.9, 5.7, <0.5 unres. Hz), 3.95 (1H, dddd, J=12.1, 6.5, 4.0, 1.2 Hz), 4.18 (1H, ddtt, J=23.5, 7.0, 5.3, 1.4 Hz), 4.35 (1H, dd, J=6.7, 5.7 Hz, 5'-OH), 5.31 (1H, dddd, J=15.7, 8.5, 4.4, 0.8 Hz), 7.34 (1H, d, J=8.3 Hz, 1-OH). $^1H$ decoupled $^{13}C$ NMR of cis 1,5-(6) (125 MHz, $CDCl_3$) δ58.3 (d, $J_{C-C-C-F}$=6.5 Hz), 74.2 (dd, $J_{C-C-F}$=26.8, 22.2 Hz), 92.2

(ddd, $J_{C-C-F}$=27.7, 19.4, 4.62 Hz). $^{19}$F decoupled $^{13}$C NMR of cis 1,5-(6) (125 MHz, CDCl$_3$) δ109.7(CF$_2$), 111.6 (CF$_2$), 113.5(CF$_2$). $^{19}$F of cis 1,5-(6) (470 MHz, d$_6$-Acetone, $^{19}$F-$^{19}$F COSY cross peak) δ−145.5 (1F, ddddtd, J=270.7, 14.7, 14.0, 9.3, 0.8 Hz), −139.4 (1F, ddddddd, J=261.1, 16.1, 14.8, 7.6, 1.42 Hz), −132.8 (1F, ddtd, J=267.5, 15.5, 9.3, 1.3 Hz), −131.7 (1F, ddddddd, J=264.5, 15.4, 13.8, 8.1, 1.4, 0.5 Hz), −130.4 (1F, ddtdd, J=264.5, 12.3, 9.4, 1.4, 0.8Hz), −125.3 (1F, ddqd, J=270.7, 13.9, 7.9, 4.0 Hz). $^1$H NMR of trans 1,5-(6) (500 MHz, d$_6$-Acetone, $^1$H-$^{19}$F HETCOR cross peak) δ3.80 (1H, dddd, J=12.1, 6.9, 5.7, <0.5 unres. Hz), 3.96, (1H, dddd, J=12.1, 6.5, 4.0, 1.2 Hz), 4.24 (1H, t, J=6.3 Hz, 5'-OH), 4.52(1H, d unres.m, J=24.8 Hz), 5.55 (1H, dt, J=7.3, 6.0 Hz), 7.36 (1H, dt, J=5.6, 2.1 Hz, 1-OH). $^1$H decoupled $^{13}$C NMR of trans 1,5-(6) (125 MHz, CDCl$_3$) δ58.2 (d, $J_{C-C-C-F}$=4.6 Hz), 69.1 (dd, $J_{C-C-F}$=26.8, 21.3 Hz), 91.6 (ddd, $J_{C-C-F}$=36.1, 23.1, 2.8 Hz). $^{19}$F decoupled $^{13}$C NMR of trans 1,5-(6) (125 MHz, CDCl$_3$) δ109.0(CF$_2$), 111.2 (CF$_2$), 11 3.5(CF$_2$) $^{19}$F of trans 1,5-(6) (470 MHz, d$_6$-Acetone, $^{19}$F -$^{19}$F COSY cross δ−1.43.9 (1F, dddddd, J=269.5, 12.8, 10.0, 8.0, Hz), −131.2 (1F, dtddd, J=263.2, 16.3, 12.6, 7.8, 1.7 Hz), −130.7 (1F, ddtdt, J=268.5, 11.6, 3.7, 1.8, 1.0, 0.5 Hz), −129.3 (1F, ddddd, J=263.2, 13.2, 9.8, 8.0, 1.8, 0.8 Hz), −123.4 (1F, dddtdd, J=269.4, 15.1, 13.2, 7.5, 2.6, 2.1 Hz), −120.7 (1F, ddddddd, J=268.5, 16.4, 15.4, 8.2, 7.3, 1.7, 0.9 Hz). Anal. Calcd. for C$_6$H$_6$F$_6$O$_3$: C, 30.01; H, 2.52. Found: C, 29.97; H, 2.44.

(6)

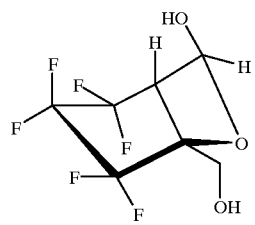

Figure 2:
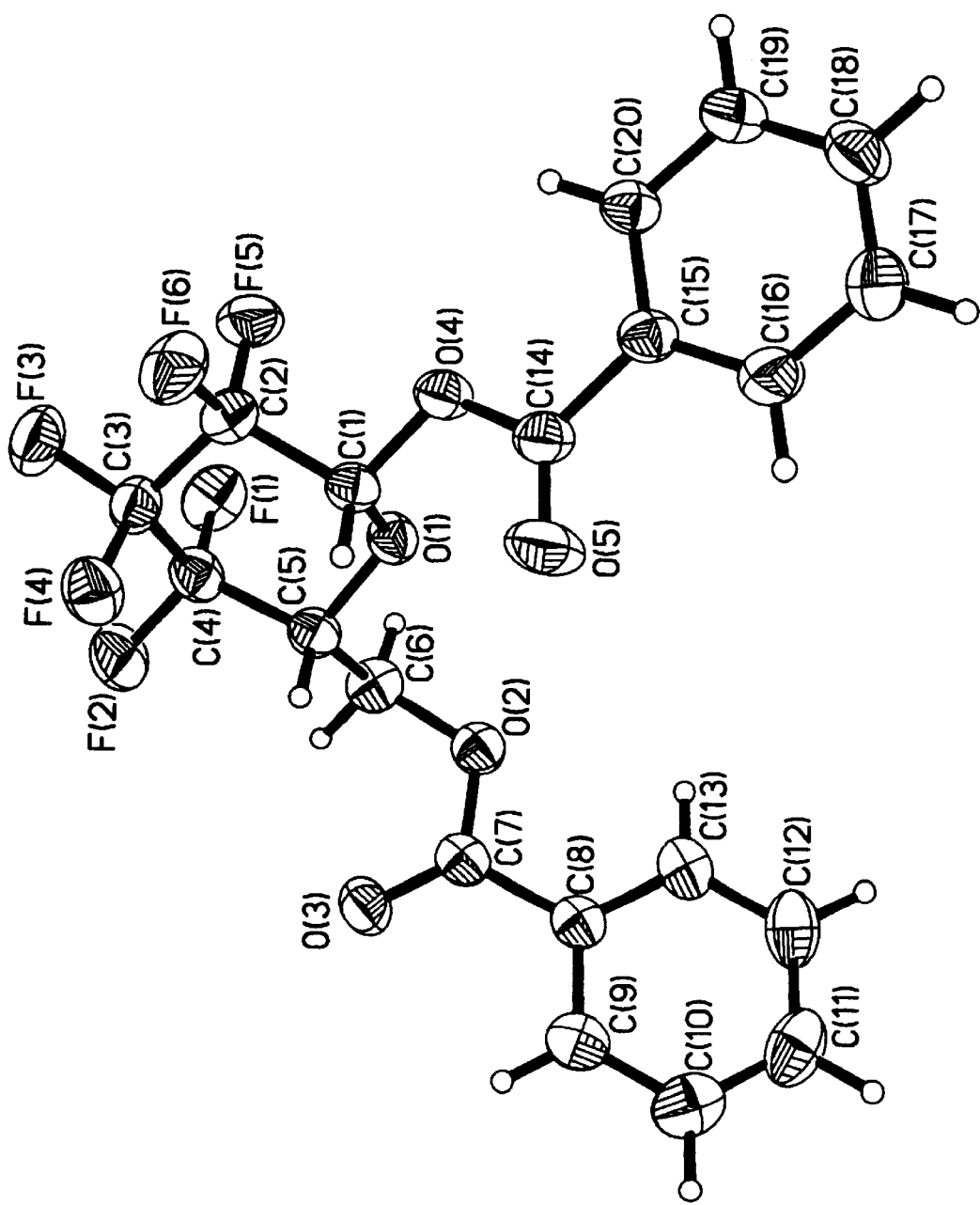
FIG. 2 shows an x-ray crystal determination of compound 7.

1-O-Benzyloxy-5-(5'-O-Benzyloxymethyl)-2,2,3,3,4,4-hexafluorooxane (7). Compound 7 (134 mg, 93%) was obtained as a pale yellow solid following the same method as for 3 using alcohol 5 (113 mg, 0.32 mmol) or diol 6. The usual workup protocol followed by column chromatography and preparative TLC with 7:1 hexane:EtOAc as the eluent gives the product which is used for chiral separation. The X-ray crystal structure determination for 7 is shown in FIG. 2. $^1$H NMR (500 Mhz, CDCl$_3$ δ4.50 (1H, dm, J=21.8 Hz), 4.61 (1H, dd, J=12.1, 6.9 Hz), 4.78 (1H, dd, J=12.1, 4.0 Hz), 6.25 (1H, dd, J=14.9, 3.6 Hz), 7.45 (2H, m), 7.50 (2H, m), 7.59 (1H, m), 7.66 (1H, m), 8.03 (2H, m), 8.12 (2H, m). $^{13}$C NMR (125 MHz, CDCl$_3$) δ59.5, 71.9 (dd, $J_{C-C-F}$=27.8, 24.1 Hz), 88.5 (ddd, $J_{C-C-F}$=29.6, 18.5, 5.6 Hz), 108.5 (CF$_2$), 110.4 (CF$_2$), 112.2 (CF$_2$), 127.3, 128.4, 128.5, 128.8, 129.9, 130.5, 133.5, 134.6, 163.4, 165.9. $^{19}$F (470 MHz, CDCl$_3$) δ−127.2 (1F, d unres.m, J=277.2 Hz), −130.4 (1F, ddtd, J=256.6, 9.9, 3.3 Hz), −132.3 (1F, dtt, J=267.3, 8.3 Hz), −133.8 (1F, ddt, J=262.3, 24.7, 8.3 Hz), −137.0 (1F, ddtd, J=262.3, 16.5, 14.9, 6.6 Hz), −146.2 (1F, d unres.m, J=273.9 Hz). Anal. Calcd. for C$_{20}$H$_{14}$F$_6$O$_5$: C, 53.58; H, 3.15. Found: C, 53.24; H, 3.19.

(7)

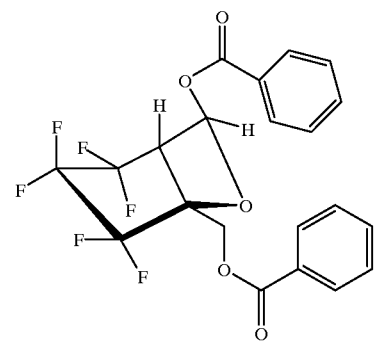

By following the same procedures as above, but employing the corresponding 2,2,3,3-terafluorodiethylbutanedioate as the starting material, the following compounds were made:

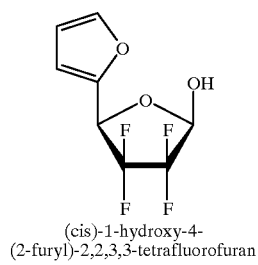

(cis)-1-hydroxy-4-(2-furyl)-2,2,3,3-tetrafluorofuran

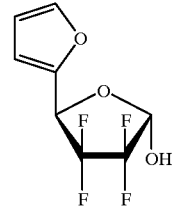

(trans)-1-hydroxy-4-(2-furyl)-2,2,3,3-tetrafluorofuran

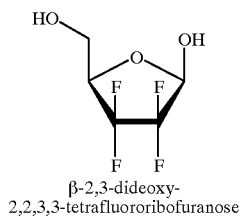

β-2,3-dideoxy-2,2,3,3-tetrafluororibofuranose

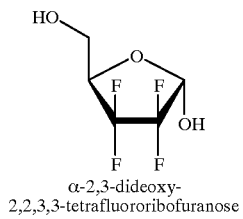

α-2,3-dideoxy-2,2,3,3-tetrafluororibofuranose

-continued

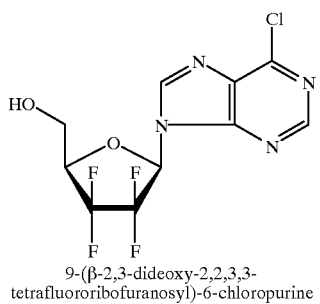

9-(β-2,3-dideoxy-2,2,3,3-
tetrafluororibofuranosyl)-6-chloropurine

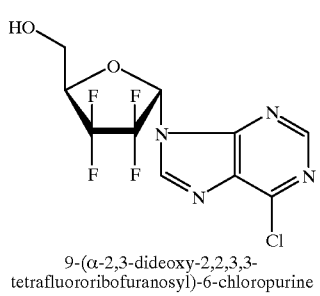

9-(α-2,3-dideoxy-2,2,3,3-
tetrafluororibofuranosyl)-6-chloropurine

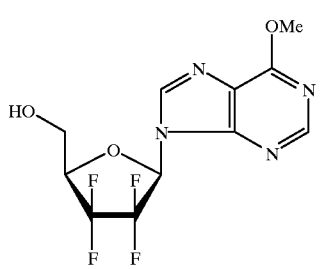

9-(β-2,3-dideoxy-2,2,3,3-
tetrafluororibofuranosyl)-6-methoxypurine

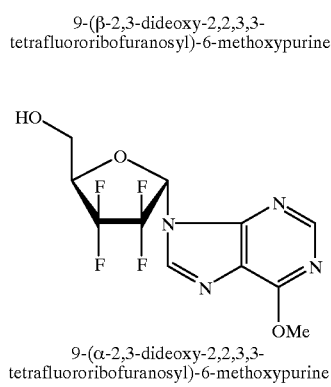

9-(α-2,3-dideoxy-2,2,3,3-
tetrafluororibofuranosyl)-6-methoxypurine

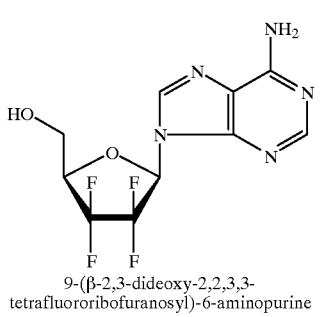

9-(β-2,3-dideoxy-2,2,3,3-
tetrafluororibofuranosyl)-6-aminopurine

-continued

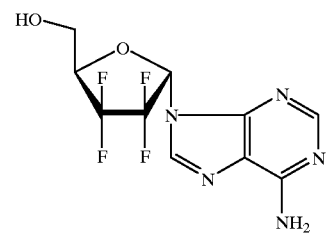

9-(α-2,3-dideoxy-2,2,3,3-
tetrafluororibofuranosyl)-6-aminopurine

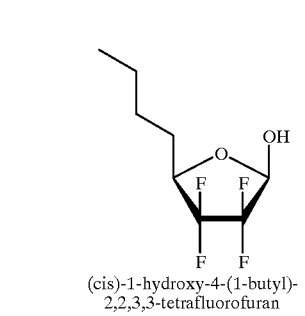

(cis)-1-hydroxy-4-(1-butyl)-
2,2,3,3-tetrafluorofuran

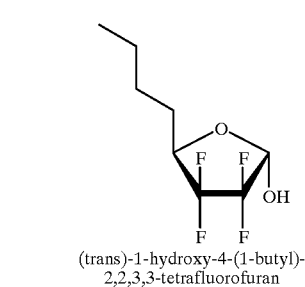

(trans)-1-hydroxy-4-(1-butyl)-
2,2,3,3-tetrafluorofuran

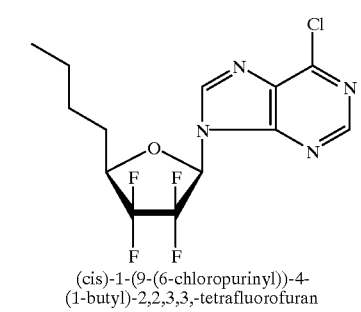

(cis)-1-(9-(6-chloropurinyl))-4-
(1-butyl)-2,2,3,3,-tetrafluorofuran

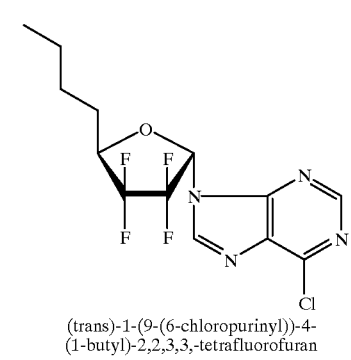

(trans)-1-(9-(6-chloropurinyl))-4-
(1-butyl)-2,2,3,3,-tetrafluorofuran

-continued

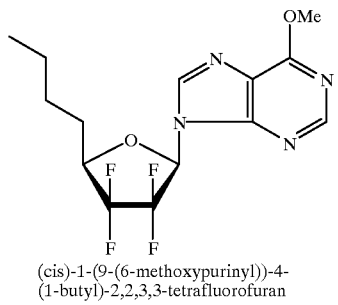

(cis)-1-(9-(6-methoxypurinyl))-4-
(1-butyl)-2,2,3,3-tetrafluorofuran

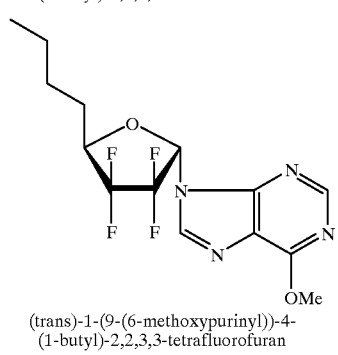

(trans)-1-(9-(6-methoxypurinyl))-4-
(1-butyl)-2,2,3,3-tetrafluorofuran

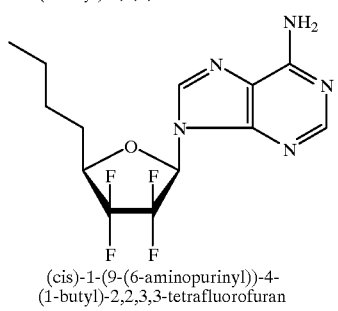

(cis)-1-(9-(6-aminopurinyl))-4-
(1-butyl)-2,2,3,3-tetrafluorofuran

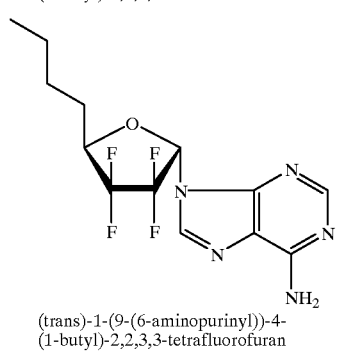

(trans)-1-(9-(6-aminopurinyl))-4-
(1-butyl)-2,2,3,3-tetrafluorofuran

In an alternative embodiment according to the present invention, starting materials for the process of the present invention of the following formula may be used:

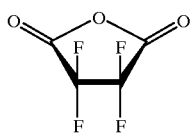

and a new reagent, benzyloxymethylzinc bromide, is used for introducing the 5'-hydroxymethyl moiety. This key reagent enables these inexpensive materials to be homologated to the proper number of carbon atoms in the ribose unit.

Compounds of the present invention are prepared according to the following scheme.

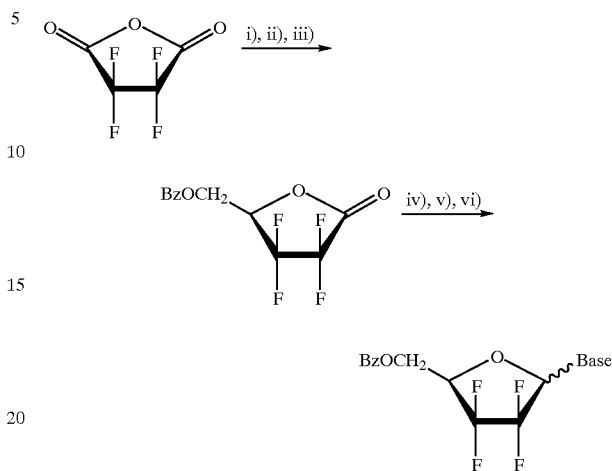

i) Benzyl-O-CH$_2$ZnBr, THF, -78° C.
ii) NaBH$_4$, 50% aq. MeOH, NaHCO$_3$
iii) DCC or POCl$_3$
iv) DIBAL-H
v) MsCl, Et$_3$N, CH$_2$Cl$_2$
vi) Silylated Base, NaI/CH$_3$CN The hexose sugar analogs according to the present invention are similarly prepared from the corresponding perfluoroglutaric anhydride.

The heavily fluorinated nucleoside analogs of the present invention may be used for the treatment of viral infections in the manner usual in the treatment of such pathologies. The compounds may be effective for the treatment of viral infections in general, and particularly in the treatment of infections caused by retroviruses, such as HIV.

The compounds may be effectively administered orally, topically or parenteraily. In general, dosages in the range of from about 0.05 mg/kg to about 5000 mg/kg are useful, preferably in the range of from about 5 mg/kg to about 500 mg/kg.

The compounds may be used in medicine in the form of conventional pharmaceutical compositions. The formulation of the compositions is conventional, and follows the usual practices of pharmaceutical chemists. When a heavily fluorinated nucleoside analog of the present invention is to be administered topically, it is formulated as a topical composition, such as a cream or ointment to be rubbed into the affected tissue. Creams are emulsions of an oily phase and an aqueous phase, in which the heavily fluorinated nucleoside analogs are dissolved or suspended. Ointments are greasy or waxy compositions, in which the nucleoside may be soluble but may be suspended, if it is insoluble at the desired concentration. Topical formulations preferably further include a transdermal agent, such as DMSO, propylene glycol, or the like.

Parenteral compositions may be preferably formulated in such a way that the heavily fluorinated nucleoside can be dissolved for injection. Alternatively, the heavily fluorinated nucleoside may be formulated as a dried powder with physiologically-acceptable suspending agents, such as starch, sugar and the like, to which sterilized water is added to form a suspension to be injected. Parenteral compositions can be formulated in aqueous bases containing moderate amounts of physiologically-acceptable solvents, such as propylene glycol and the like, and such compositions may be capable of dissolving the present heavily fluorinated nucleoside analogs at acceptable concentrations.

A great many types of orally administered compositions are in common use, including unit dosage forms such as tablets and capsules, and liquid dosage forms such as suspensions. In general, unit dosage forms are preferred in pharmacy and are formulated in such a way as to provide the usual dose in one or a small number of tablets or capsules. The formulation of tablets, making use of appropriate lubricants, binding agents and disintegration agents, is and long has been thoroughly understood by pharmaceutical chemists. The formulation of capsules involves only the dilution of the heavily fluorinated nucleoside analogs with an appropriate proportion of an inert powdery substance, such as lactose, to provide the proper bulk to fill the desired size of capsule.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

What is claimed is:

1. A compound according to formula (II):

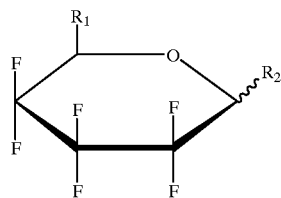

wherein $R_1$ is selected from —$CH_2$—NH-peptide, or —$CH_2$—O-peptide;

wherein $R_2$ is selected from hydroxy, —O-carbohydrate, —NH-peptide,

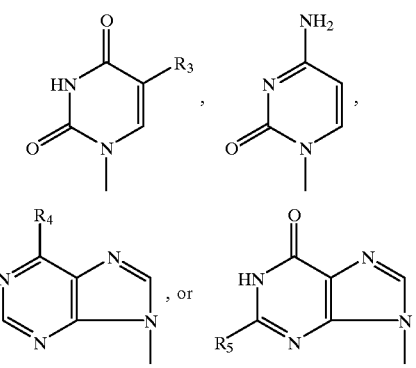

wherein $R_3$ is selected from H, halogen, lower alkyl, lower alkenyl, lower haloalkyl, lower haloalkenyl, amino, mono- or di-lower alkylamino;

wherein $R_4$ is selected from amino, hydroxy, alkoxy, or halogen; and wherein $R_5$ is H or amino including all stereoisomers thereof.

2. The compound according to claim 1 wherein $R_2$ is

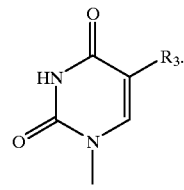

3. The compound according to claim 2 wherein $R_3$ is lower alkyl.

4. The compound according to claim 3 wherein $R_3$ is methyl.

5. The compound according to claim 3 wherein $R_3$ is ethyl.

6. The compound according to claim 2 wherein $R_3$ is lower halo alkyl.

7. The compound according to claim 6 wherein $R_3$ is trifluoromethyl.

8. The compound according to claim 2 wherein $R_3$ is bromoethenyl.

9. The compound according to claim 2 wherein $R_3$ is monoloweralkylamino.

10. The compound according to claim 9 wherein $R_3$ is methylamino.

11. The compound according to claim 2 wherein $R_3$ halogen.

12. The compound according to claim 11 wherein $R_3$ is iodo.

13. The compound according to claim 11 wherein $R_3$ is fluoro.

14. The compound according to claim 1 wherein $R_2$ is

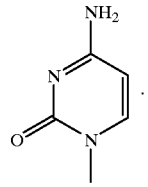

15. The compound according to claim 1 wherein $R_2$ is

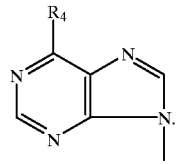

16. The compound according to claim 15 wherein $R_4$ is hydroxy.

17. The compound according to claim 15 wherein $R_4$ is amino.

18. The compound according to claim 1 wherein $R_2$ is

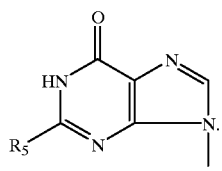

19. The compound according to claim 18 wherein $R_5$ is amino.

20. The compound according to claim 18 wherein $R_5$ is H.

21. A compound according to formula (II):

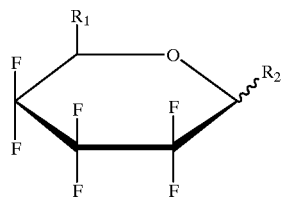

wherein
$R_1$ is selected from —$CH_2$—NH-peptide, or —$CH_2$—O-peptide;
wherein $R_2$ is —NH-peptide,

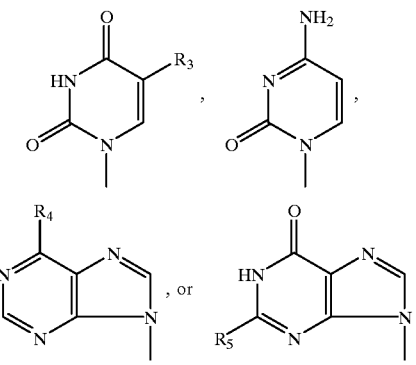

wherein
$R_3$ is selected from H, halogen, lower alkyl, lower alkenyl, lower haloalkyl, lower haloalkenyl, amino, mono- or di-lower alkylamino;
wherein $R_4$ is selected from amino, hydroxy, alkoxy, or halogen; and
wherein $R_5$ is H or amino including all stereoisomers thereof.

22. The compound according to claim 21 wherein $R_2$ is

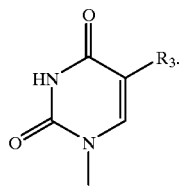

23. The compound according to claim 22 wherein $R_3$ is lower alkyl.

24. The compound according to claim 23 wherein $R_3$ is methyl.

25. The compound according to claim 23 wherein $R_3$ is ethyl.

26. The compound according to claim 22 wherein $R_3$ is lower halo alkyl.

27. The compound according to claim 26 wherein $R_3$ is trifluoromethyl.

28. The compound according to claim 22 wherein $R_3$ is bromoethenyl.

29. The compound according to claim 22 wherein $R_3$ is monoloweralkylamino.

30. The compound according to claim 29 wherein $R_3$ is methylamino.

31. The compound according to claim 22 wherein $R_3$ halogen.

32. The compound according to claim 31 wherein $R_3$ is iodo.

33. The compound according to claim 31 wherein $R_3$ is fluoro.

34. The compound according to claim 21 wherein $R_2$ is

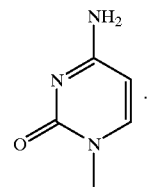

35. The compound according to claim 21 wherein $R_2$ is

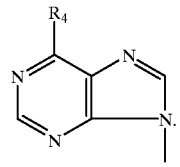

36. The compound according to claim 35 wherein $R_4$ is hydroxy.

37. The compound according to claim 35 wherein $R_4$ is amino.

38. The compound according to claim 21 wherein $R_2$ is

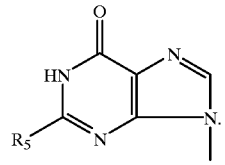

39. The compound according to claim 38 wherein $R_5$ is amino.

40. The compound according to claim 38 wherein $R_5$ is H.

* * * * *